United States Patent [19]
Armington et al.

[11] Patent Number: 5,727,499
[45] Date of Patent: Mar. 17, 1998

[54] LIGHTWEIGHT DISPOSABLE KITTY LITTER BOX

[75] Inventors: Steven E. Armington, Gates Mills; Carl V. Santoiemmo, Highland Heights; Dale Panasewicz, Strongsville, all of Ohio

[73] Assignee: Ranpak Corp., Concord Township, Ohio

[21] Appl. No.: 466,253

[22] Filed: Jun. 6, 1995

Related U.S. Application Data

[63] Continuation-in-part of Ser. No. 125,310, PCT/US93/11085 filed on Nov. 19, 1993, abandoned.

[51] Int. Cl.[6] .................................................. A01K 29/00
[52] U.S. Cl. .................................................. 119/168
[58] Field of Search .................................. 119/165, 166, 119/167, 168

[56] References Cited

U.S. PATENT DOCUMENTS

| | | | |
|---|---|---|---|
| 3,675,625 | 7/1972 | Miller et al. | 119/173 |
| 4,532,890 | 8/1985 | Ohki et al. | 119/172 |
| 4,607,594 | 8/1986 | Thacker | 119/172 |
| 4,997,091 | 3/1991 | McCrea | 206/584 |
| 5,100,600 | 3/1992 | Keller et al. | 119/173 X |
| 5,173,352 | 12/1992 | Parker | 428/174 |
| 5,465,686 | 11/1995 | Monetti et al. | 119/168 |
| 5,482,007 | 1/1996 | Kumlin | 119/169 |

Primary Examiner—Thomas Price
Attorney, Agent, or Firm—Renner, Otto, Boisselle & Sklar, P.L.L.

[57] ABSTRACT

A lightweight disposable kitty litter box comprises a container which forms a closed receptacle (110) and fresh kitty litter (20) which is enclosed within the closed receptacle (122). The kitty litter (20) comprises a resilient paper product having a density between 0.01 and 0.10 ounces per cubic inch. The container is convertible between a closed condition in which it forms a closed receptacle (110) and an open condition in which it forms an open receptacle (122). To supply a kitty litter box for a cat, the container is converted into the open condition to form the open receptacle to thereby allow the cat access to the fresh kitty litter (20). The cat may then interact with the fresh kitty litter (20) until it reaches a sanitarily unacceptable state. The sanitarily unacceptable kitty litter is then enclosed in the closed container by converting the container into the closed condition. The container and the sanitarily unacceptable kitty litter enclosed therein may then be disposed as a unit.

30 Claims, 12 Drawing Sheets

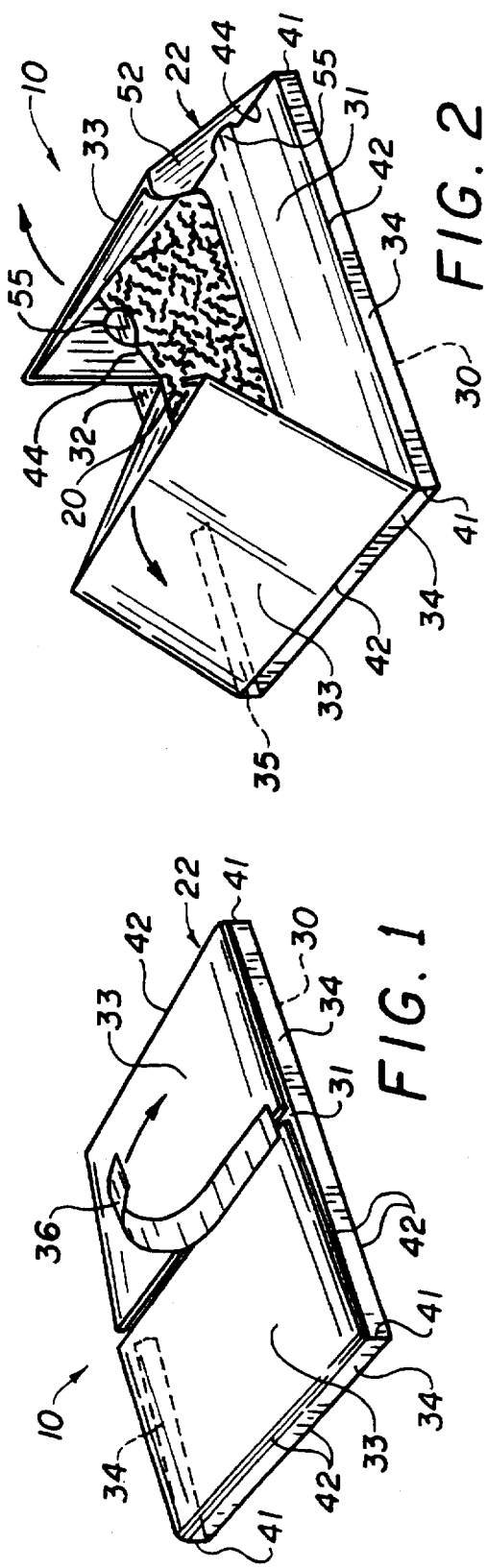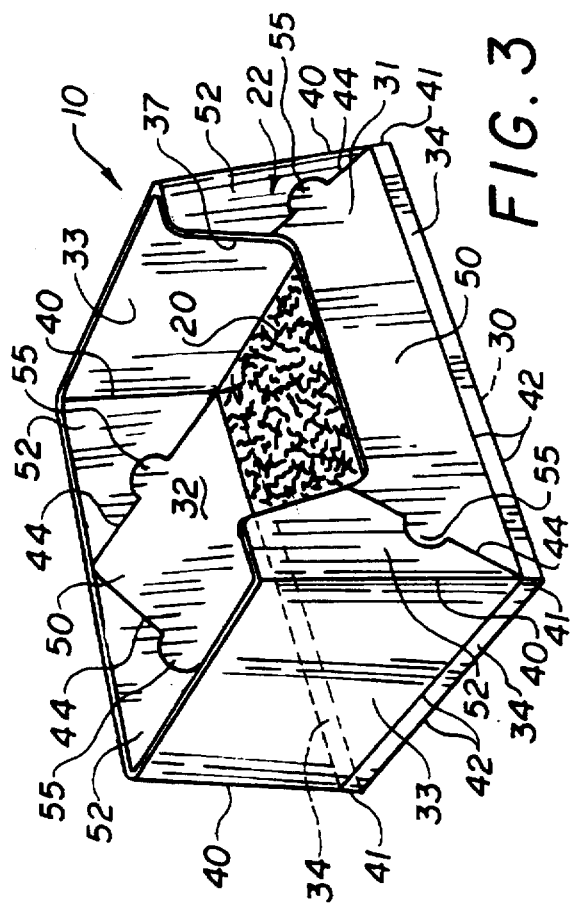

LIGHTWEIGHT DISPOSABLE KITTY LITTER BOX

RELATED APPLICATIONS

This application is a continuation of PCT/US93/11085 filed Nov. 19, 1993, which is a C-I-P of U.S. Ser. No. 08/125,310, filed Sep. 22, 1993, now abandoned. The entire disclosure of this prior application is hereby incorporated by reference herein.

FIELD OF THE INVENTION

This invention relates generally as indicated to a lightweight disposable kitty litter box. More particularly, the present invention relates to a lightweight kitty litter box which includes a container and fresh kitty litter enclosed within the container. The fresh kitty litter comprises a resilient paper product. The container is designed so that the kitty litter box may be compactly stored as a closed receptacle until ready for use, converted into an open receptacle for interaction with a cat, and then converted back into a closed receptacle for convenient and sanitary disposal purposes.

BACKGROUND OF THE INVENTION

A kitty litter box is commonly used to accommodate the daily functions of a cat. The upkeep of a kitty litter box is crucial to the comfort of a cat and/or the enjoyment of a cat by the pet's owner. Specifically, a cat will interact with the kitty litter while relieving its bodily needs. Thus, after a period of time, the kitty litter will reach a sanitarily unacceptable condition. At this point, the cat may reject the kitty litter box and instead seek alternate locations, such as rugs, floors, furniture, and plants. Additionally, the sanitarily unacceptable kitty litter will often produce an undesirable odor and may be of a non-hygienic nature. Consequently, a cat owner must be extremely conscientious about replacing kitty litter on a timely basis.

In the past, a cat's kitty litter needs were addressed by pouring a granular absorbent material, such as a processed clay product, into a clean open receptacle. The cat would then interact with the fresh kitty litter until it reached a sanitarily unacceptable state. The open receptacle was then emptied, such as by transferring the sanitarily unacceptable kitty litter into a plastic bag and then disposing of the plastic bag. Additionally, the open receptacle would have to be washed at least on a periodic basis to eliminate undesirable odors and to promote hygienics. The open receptacle would then be re-filled with fresh kitty litter for further interaction with the cat.

The odor and the non-hygienic nature of sanitarily unacceptable kitty litter often makes the task of "cleaning the litter box" an unpleasant experience. This unpleasantness is multiplied in situations where a large number of kitty litter boxes are needed, such as at pet shops, animal shelters and/or pet shows. Additionally, some experts believe that contact with sanitarily unacceptable kitty litter may impose certain health risks on pregnant women. Moreover, traveling with a cat often involves the inconvenient and cumbersome chore of transporting the supplies for a cat's kitty litter needs (i.e., the open receptacle and the fresh kitty litter).

A relevant recent development is "scoopable" kitty litter. With this type of kitty litter, the portions of the litter that interacted with the cat form clumps. These clumps are removed from the open receptacle, such as by scooping them into a plastic bag and disposing of the plastic bag. While "scoopable" kitty litter minimizes the need to completely replace kitty litter, it still requires at least limited contact with the sanitarily unacceptable kitty litter. Additionally, the open receptacle must still be completely emptied and cleaned on a periodic basis.

Another relevant recent development is disposable kitty litter boxes, such as those disclosed in U.S. Pat. Nos. 5,203,282 to Hasiuk; 5,144,914 to Giannakopoulos; 5,117,781 to Roach; 5,080,043 to Fields; 4,890,576 to James; 4,553,671 to Cheesman; 3,886,901 to Zeitter; 3,581,977 to Kirsky; and 3,154,052 to Sweeney. With particular reference to the kitty litter boxes disclosed in the James, Zeitter and Sweeney patents, they each include a container and a granular kitty litter enclosed within the container. Such a container is designed to be stored as a closed receptacle until ready for use, converted into an open receptacle for interaction with a cat, and then converted back into a closed receptacle for convenient and sanitary disposal purposes. Thus, the James, Zeitter and/or Sweeney kitty litter boxes would seem to eliminate the often unpleasant and non-hygienic task of changing kitty litter.

Two significant drawbacks are found in the disposable kitty litter boxes disclosed in the above-identified patents. The first drawback relates to the weight of such litter boxes. Specifically, the amount of granular material necessary to accommodate most kitty litter boxes can create a heavy burden during the transfer of a fresh kitty litter box to the desired location and during the disposal of the kitty litter box. The weight further detracts from the nestability and stackability of these litter boxes. A second significant drawback results from the "non-resilient" nature of most granular kitty litter products which require a bulky packaging arrangement to accommodate the desired volume of material. As with the weight factor, the non-resilient nature detracts from the nestability and stackability of the previously disclosed litter boxes. Consequently, the weight and size parameters of these kitty litter boxes often nullifies their convenience in connection with disposal.

Accordingly, a need remains for a lightweight nestable and stackable kitty litter box which totally eliminates the often unpleasant and non-hygienic task of changing kitty litter. Additionally, in view of our planet's already critical waste disposal problems, applicants believe that a need remains for a kitty litter box which incorporates biodegradable and recyclable materials.

SUMMARY OF THE INVENTION

The present invention provides a disposable kitty litter box which totally eliminates the often unpleasant and sometimes unsanitary task of changing kitty litter. The kitty litter box contains a lightweight resilient kitty litter, whereby the box's weight and size parameters do not overcome its convenience in connection with disposal. Additionally, the kitty litter box may incorporate biodegradable and recyclable material, thereby making it an environmentally responsible product.

More particularly, the present invention provides a disposable kitty litter box comprising a lightweight container and fresh kitty litter which may be enclosed within the container. The container is convertible between a closed condition, in which it forms a closed receptacle, and an open condition in which it forms an open receptacle. The container is preferably made of a paper product, such as corrugated cardboard, and thus is biodegradable and recyclable.

In one embodiment the container comprises an open receptacle having a relatively large, flat bottom panel, and four slightly outwardly extending but at least substantially vertical sides, and a separate flat cover having an area slightly smaller than, but substantially coextensive with, the inside dimensions of the walls forming the open receptacle. Thus, the separate flat cover panel forms a lid, enclosing the resilient kitty litter of the present invention within the open receptacle, thereby forming the container. In this embodiment, the receptacle walls extend vertically outward slightly so as to enable and facilitate nestable stacking of the containers.

The fresh kitty litter comprises a resilient paper material having a density between 0.01 and 0.100 ounces per cubic inch and more preferably a density of approximately 0.035 ounces per cubic inch when the container is in a closed condition. The resilient nature of the kitty litter allows a compact packaging arrangement to accommodate the desired volume of material. Additionally, the density characteristics of the kitty litter allows an unburdensome transfer of the kitty litter box to the desired location and/or disposal of the used kitty litter box. Preferably, the paper material comprises a plurality of paper strips and more preferably the paper material comprises a plurality of paper strips compressed in an accordion-like fashion. Preferably, the kitty litter is biodegradable and recyclable.

In both preferred embodiments, the container, when empty, weighs approximately one pound, and the completed kitty litter box (i.e., the fresh kitty litter and the container enclosing the litter) weighs approximately one and one-half pounds. By way of comparison, applicants' testing has proven that if the preferred container was filled with a conventional clay litter, either of the conventional or "scoopable" type, it would weigh approximately from seven to nine pounds. Thus, the present invention provides a kitty litter box which reflects a very significant reduction in weight as compared to previous litter boxes. Applicants note that this comparison may be somewhat conservative because it may actually require a greater volume of clay litter to replace the resilient paper kitty litter.

The present invention also provides a method for supplying a kitty litter box for a cat. In this method, the container (with the fresh resilient low-density paper kitty litter enclosed therein) is converted into the open condition to form the open receptacle. In this manner, the cat is allowed to access the fresh kitty litter and may interact with the fresh kitty litter until it reaches a sanitarily unacceptable state. The sanitarily unacceptable kitty litter is then enclosed by converting the container into the closed condition. The container, and the sanitarily unacceptable kitty litter enclosed therein, may then be disposed as a unit.

A kitty litter box according to the present invention may be used to replace conventional kitty litter boxes in the homes of cat owners. Also, the kitty litter box of the present invention would be advantageous in situations where a large number of kitty litter boxes are needed, such as at pet shops, animal shelters, and/or pet shows. Moreover, the kitty litter box is especially suited for traveling with cats. One disclosed embodiment provides a kitty litter box which is stackable and nestable, increasing its utility in situations calling for a large number of such kitty litter boxes, and reducing storage requirements generally.

An absorbent, antibacterial sheet is included with the disclosed kitty litter box. This sheet provides increased absorbency and protection from the spread of harmful bacteria associated with the use by a cat of the disclosed kitty litter box.

Both the absorbent sheet and the fresh kitty litter may be treated either or both a broad spectrum antibiotic compound and an odor reducing agent. The broad spectrum antibiotic or antibacterial compound may be added to retard growth of bacteria and thereby increase the sanitary useful life of the kitty litter box. The odor reducing or neutralizing agent is added to reduce or eliminate odors associated with the intended use of the kitty litter box. In addition, a fragrance may be added in order to mask odors associated with the kitty litter box.

These and other features of the invention are fully described and particularly pointed out in the claims. The following descriptive annexed drawings set forth in detail two illustrative embodiments of the invention. However, these embodiments are indicative of but two of the various ways in which the principles of the invention may be employed.

BRIEF DESCRIPTION OF THE DRAWINGS

In the annexed drawings:

FIG. 1 is a perspective view of a disposable kitty litter box according to an embodiment of the present invention, the kitty litter box including a container which is convertible between a closed condition in which it forms a closed receptacle and an open condition in which it forms an open receptacle, the container being shown in the closed condition;

FIG. 2 is a perspective view of an embodiment of the kitty litter box with the container being shown in a partially opened condition;

FIG. 3 is a perspective view of an embodiment of the kitty litter box with the container being shown in the open condition;

DETAILED DESCRIPTION

Figure 4:
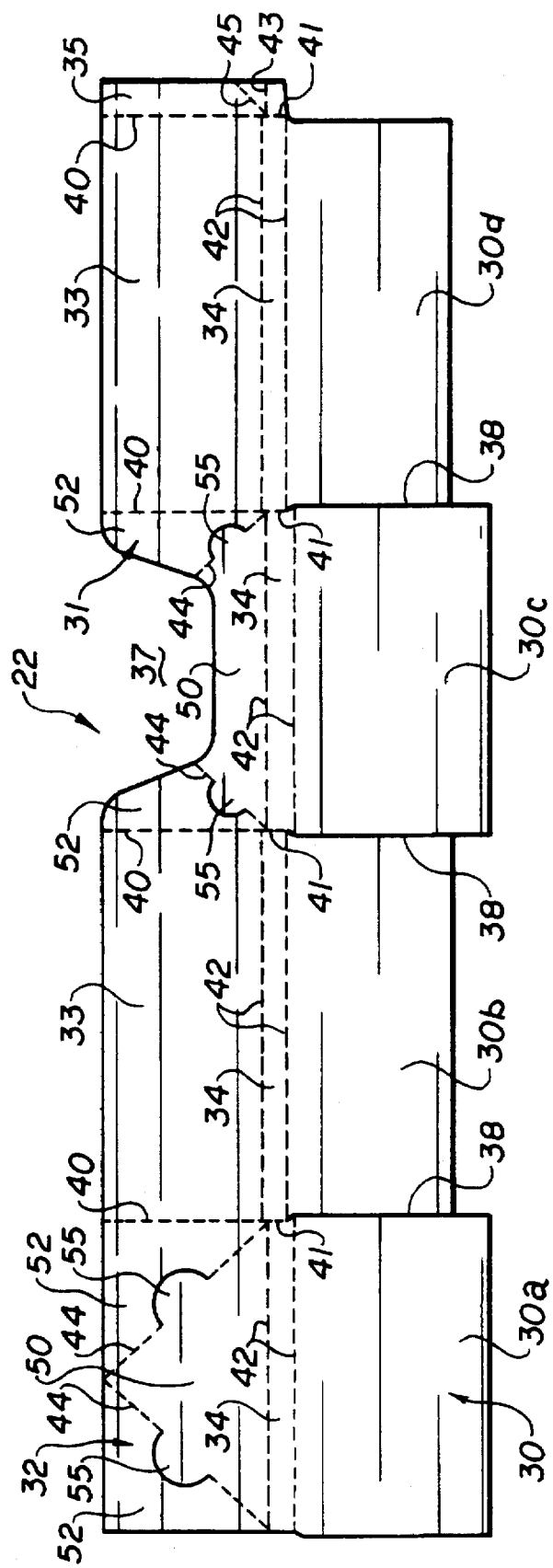
FIG. 4 is a plan view of a single sheet of cardboard from which an embodiment of the container can be assembled.

Referring now to the drawings in detail and initially to FIGS. 1–3, a disposable kitty litter box 10 according to the present invention is shown. The kitty litter box 10 includes fresh kitty litter 20 enclosed within a container 22. As is explained in more detail below, the container 22 is designed so that the kitty litter box 10 may be compactly stored as a closed receptacle until ready for use, converted into an open receptacle for interaction with a cat, and then converted back into a closed receptacle for convenient and sanitary disposal purposes. Although not specifically shown in these drawings, the kitty litter box 10 preferably includes an anti-bacterial pad which is positioned at the bottom of the container.

In one preferred embodiment, the fresh kitty litter comprises a paper product so that it is biodegradable and recyclable, and thus environmentally responsible. More preferably the fresh kitty litter 20 comprises the paper product disclosed in U.S. Pat. Nos. 5,088,972; 5,134,013 and 5,173,352; and U.S. patent application Ser. Nos. 07/861,225 and 07/971,046. (All of these patents/applications are assigned to the assignee of the present invention and their entire disclosures are hereby incorporated by reference.) This paper product comprises a plurality of accordion-folded strips which are preferably made of thirty-pound kraft paper. The strips are preferably treated with an odor reducing or neutralizing agent. The strips may also include a fragrance compound to mask odors. Additionally, the strips may be treated with an antibiotic or antibacterial material. The odor reducing or neutralizing agent and the antibiotic or antibacterial material are described more fully below.

The fresh kitty litter 20 is a resilient paper material having a density between 0.01 and 0.100 ounces per cubic inch and more preferably a density of approximately 0.035 ounces per cubic inch whereby the box's weight and size parameters do not nullify its convenience in connection with disposal. In this preferred embodiment, the container 22, when empty, weighs approximately one pound, and the completed kitty litter box 10 (i.e., the fresh kitty litter 20 and the container 22 enclosing the litter) weighs approximately one and one-half pounds. By way of comparison, applicants' testing has proven that if the preferred container 22 was filled with a conventional clay litter, it would weigh approximately from eight to nine pounds. Also by way of comparison, applicants' testing has proven that if the preferred container 22 was filled with "scoopable" clay litter, it would weigh approximately from six to eight pounds. Thus, the present invention provides a kitty litter box which reflects a significant decrease in weight. Applicants note that this comparison may be somewhat conservative because it may actually require a greater volume of clay litter and/or "scoopable" litter to replace the resilient paper kitty litter 20. Applicants contemplate a depth of their fresh, resilient, low-density kitty litter of about one and one-half inches, whereas conventional clay kitty litters call for a depth of two inches. In the above described comparative testing, applicants' containers were filled only to a depth of one and one-half inches with, respectively, the fresh kitty litter of the present invention and clay kitty litter.

As was indicated above, in this embodiment the container 22 is convertible between a closed condition in which it forms a closed receptacle (FIG. 1) and an open condition in which it forms an open receptacle (FIG. 3). When the container 22 is initially in the closed condition, the fresh kitty litter 20 is enclosed within the closed receptacle. When the container 22 is in the open condition, the open receptacle confines the kitty litter 20 while at the same time permitting a cat access for interaction with the kitty litter 20.

Thus, to supply a kitty litter box for a cat, the container 22 is converted into an open receptacle to thereby permit access to the fresh kitty litter 20. The cat may then interact with the fresh kitty litter 20 until it reaches a sanitarily unacceptable condition. Once the fresh kitty litter 20 reaches a sanitarily unacceptable condition, the container 22 is converted back into the closed receptacle to thereby enclose the sanitarily unacceptable kitty litter within the container 22. The container 22, and the sanitarily unacceptable kitty litter enclosed therein, may then be disposed of as a unit. In this manner, the often unpleasant and unsanitary task associated with changing kitty litter in conventional boxes is eliminated.

The container 22 is made of material which is of a sufficient strength to function as a self-standing carton in its open condition and of sufficient flexibility to convert between the open and the closed condition. Preferably, the container 22 is made of a paper material so that it is biodegradable and recyclable, and thus environmentally responsible. More preferably, the container 22 is made of corrugated cardboard as this material economically provides the desired characteristics.

The conversion is accomplished by the container 22 including a set of panels and appropriate interconnections therebetween. Specifically, when viewed in the open condition (FIG. 3), the container 22 comprises a bottom panel 30 which, as is explained in more detail below, is formed from four separate sections 30a, 30b, 30c, and 30d. The container 22 additionally comprises a front panel 31, a rear panel 32, two side panels 33, and four connecting panels 34. The container 22 further comprises a coupling panel 35 which is not visible in the perspective shown in FIGS. 1–3 but is explained in more detail below in connection with FIG. 4.

When the container 22 is in the closed condition (see FIG. 1), the panels 31–33 are in a horizontal orientation and form a closed receptacle for the kitty litter 20. The closed receptacle has a width $w_{closed}$, a length $l_{closed}$, and a height $h_{closed}$. In this preferred embodiment, these dimensions are approximately fifteen inches, eighteen inches, and one and a half inches.

When the container 22 is in an open condition (see FIG. 3), the panels 30–36 form the open receptacle. The open receptacle has a width $w_{open}$ which is equal to $w_{closed}$, a length $l_{open}$ which is equal to $l_{closed}$, and a height $h_{open}$ which is substantially greater than $h_{closed}$. Specifically, the height $h_{open}$ is approximately nine inches. Thus, the volume of the container 22 when it is in the open condition (or the open receptacle) is greater than when it is in the closed condition (or the closed receptacle).

As is best seen in FIG. 1, the height of each of the side panels 33 ($h_{closed}$–$h_{open}$) is preferably such that it equals approximately half of the width $w_{closed}$ or $w_{open}$. (Thus, in this preferred container 22, the height of the side panels would be approximately seven and a half inches.) In this manner, the free edges of the side panels 33 abut when the container 22 is in the closed condition. The kitty litter box 10 may additionally include an adhesive strip 36 for locking these edges together and securing the container 22 in the closed condition.

Referring now additionally to FIG. 4, a single sheet of cardboard from which the container 22 may be constructed is illustrated. As shown, the panels 30–35 are all roughly rectangular in shape with the front panel 31 including a cut-out 37. As is best seen by referring briefly back to FIG. 3, the cut-out 37 forms an entrance-way into the open receptacle when the container 22 is in the open condition. In the single sheet of cardboard, the rear panel 32, one of the side panels 33, the front panel 31, the other side panel 33, and the coupling panel 35 are arranged linearly adjacent to each other in this order. The corresponding connecting panels 34 are arranged in a similar manner below the panels 31–33. The sections 30a, 30b, 30c, and 30d of the bottom panel 30 are connected to the lower edges of the connecting panels 34 (but not the coupling panel 35) and are separated by cut lines 38.

The interconnections of the container 22 comprise panel-joining hinges (i.e., hinges which join separate panels together) and panel-internal hinges (i.e., hinges within a particular panel). The panel-joining hinges include vertical fold lines 40 and 41. Four of these vertical fold lines, namely fold lines 40, connect the rear panel 32 to the adjacent side panel 33, this side panel 33 to the front panel 31, the front panel 31 to the other side panel 33, and the latter side panel 33 to the coupling panel 35. The connecting panels 34 include similar vertical fold lines 41 therebetween. As is best seen by referring briefly back to FIG. 3, the fold lines 40 and 41 together form the corner intersections of the container 22 when it is in an open condition.

The panel-joining hinges of the container 22 additionally comprise nine horizontal fold lines 42 and 43. Eight of these fold lines, namely fold lines 42, are arranged in parallel pairs along the upper and lower edges of the connecting panels 34. Thus, each of the upper fold lines 42 joins the front/rear/side panel 31/32/33 to the corresponding connecting panel 34 while the lower fold lines 42 join the appropriate section of the bottom panel 30 to the corresponding connecting panel 34. The remaining horizontal fold line 43 is located on the coupling panel 35 and is aligned with the upper fold line 42 on the adjacent connecting panel 34.

The panel-internal hinges of the container 22 comprise five slanted fold lines 44 and 45. Four of these slanted lines, namely fold lines 44, extend from the bottom corners of the front/rear panels 31 and 32 at an approximately 45° angle and separate each of the panels 31 and 32 into a middle portion 50 and outer portions 52. In the rear panel 32, the outer portions 52 are isosceles triangles and the middle portion 50 is a complementary triangle. The portions on the front panel 31 are similar in shape except that they are truncated by the cut-out 37. In the preferred embodiment, the fold lines 43 are interrupted by a semi-circular cut-out forming a semi-circular locking tab 55. The remaining slanted fold line 45 is arranged on the coupling panel 35 so that it will overlay the outer fold line 44 of the rear panel 32 in the assembled container 22.

To assemble the container 22 from the sheet of cardboard, the panels 30–35 are hinged about the vertical fold lines 40 and 41 to form perpendicular corner intersections. The coupling panel 35 is then positioned beneath the free vertical edge of the rear panel 32 and secured thereto by a suitable method, such as adhesives. The sections 30a and 30c of the bottom panel 30 are then hinged inward about the adjacent fold lines 42. Thereafter, the sections 30b and 30d of the bottom panel are hinged inward about the adjacent fold lines 42 and over the sections 30a and 30c. Preferably, the bottom sections 30c and 30d are dimensioned so that their distal edges will abut in this folding arrangement. In any event, the bottom sections 30c and 30d are secured together by an appropriate means, such as a strip of adhesive tape (not shown). The container 22 is then in the open condition and may be filled with the kitty litter 20. If an anti-bacterial pad is used, it would be inserted into the container 22 prior to filling the container 22 with the kitty litter 20.

To convert the container 22 to the closed condition, the middle portions 50 of the front/rear panels 31/32, the outer portions 52 of the front/rear panels 31/32, and the side panels 33 are positioned in a horizontal orientation. Specifically, the outer portions 52 are folded over the middle portions 50 and the side panels 33 are positioned over the outer portions 52. In this folding arrangement, the middle portions 50 of the front/rear panels 31/32 extend inward from the fold lines 42 at an approximately 90° angle; the outer portions 52 extend inward from the slanted fold lines 45 at a 180° angle and extend inward from the panel-joining folds 40 at a 180° angle; and the side panels 33 extend inward from the fold lines 42 at a 90° angle. (Note that the fold lines 42 and 45 of the coupling panel 35 accommodate this folding pattern.) Thus, the side panels 33 form the top surface of the container 22 when it is in the closed condition.

To convert the container 22 from the closed condition to the open condition, the adhesive strip 36 is removed. (See FIG. 1.) The side panels 33 are then manually pulled upward and outward to an upright vertical position. (See FIG. 2 which, while showing the container 22 only partially opened, best illustrates this concept.) This manual pulling simultaneously unfolds the outer and middle portions 50 and 52 of the front/rear panels 31 and 32 and forces the front/rear panels to a vertical position. When the panels 31–33 are in an upright vertical position, the container 22 forms the open receptacle to thereby permit access to the fresh kitty litter 20. A cat may then interact with the fresh kitty litter 20 by entering the kitty box 10 through the cut-out 37. If the container 22 includes locking tabs 55, they may be maneuvered to lock the panels 31–33 in the upright vertical position.

Once the fresh kitty litter 20 reaches a sanitarily unacceptable condition, the container 22 may be converted back into the closed receptacle by releasing the locking tabs 55 and manually pushing the side panels 33 inward and downward. This manual pushing simultaneously folds the outer and middle portions 50 and 52 of the front/rear panels 31 and 32 and forces the front/rear panels to a horizontal position. The adhesive strip 60 (or another similar strip) may then be used to re-secure the free edges of the side panels 33 thereby sealing the sanitarily unacceptable kitty litter within the container 22. The container 22, and the sanitarily unacceptable kitty litter enclosed therein, may then be disposed of as a unit.

Figure 5:
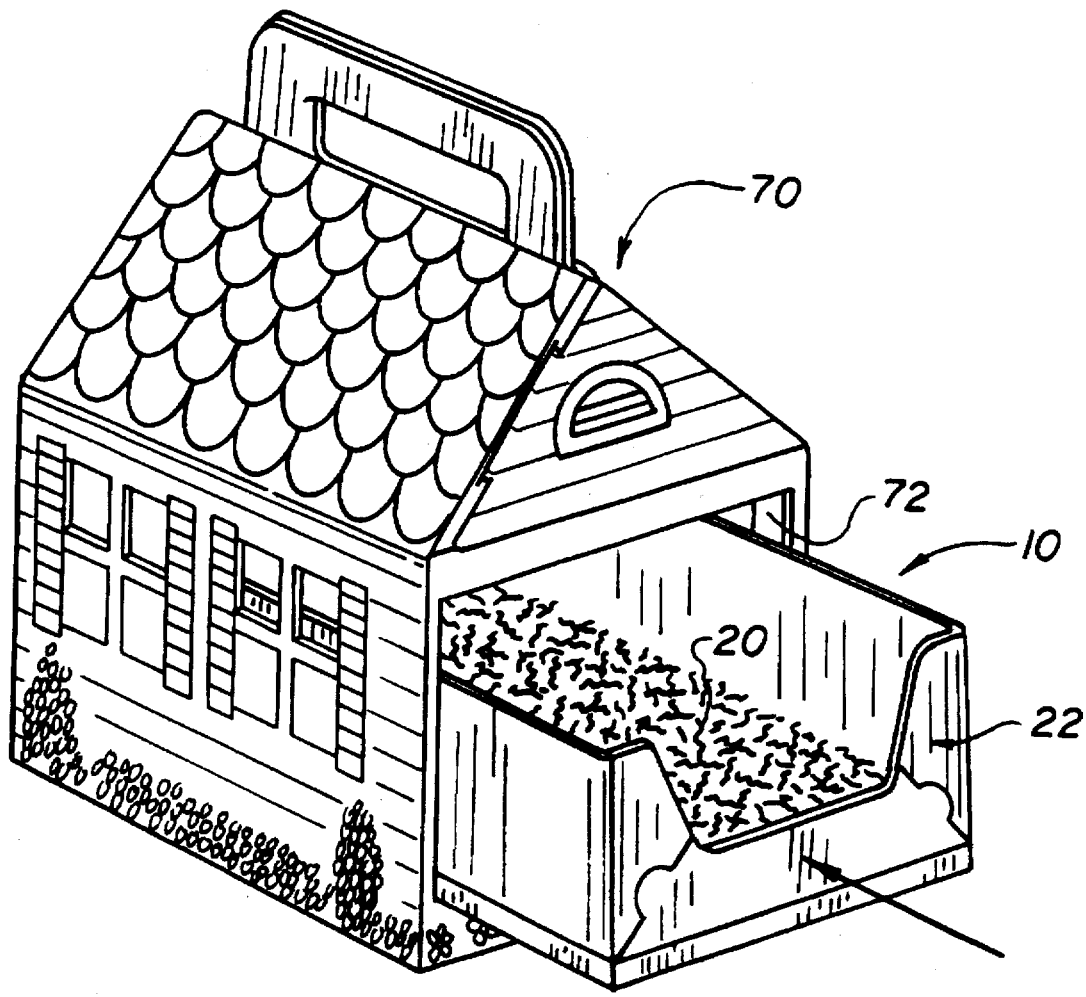
FIG. 5 is a perspective view of a decorative housing for an embodiment of the kitty litter box, the kitty litter box (in an open condition) being shown partially inserted into the housing.
Figure 6:
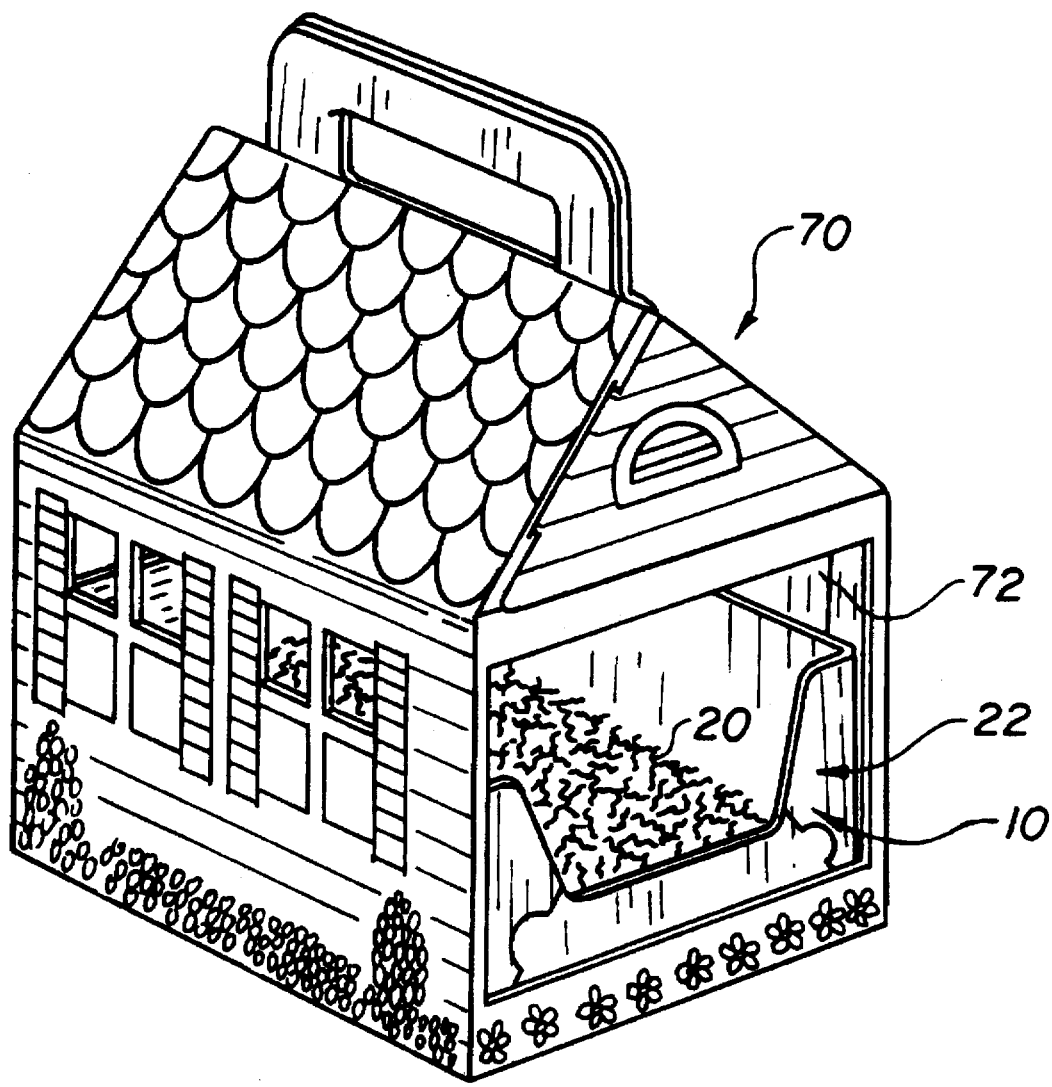
FIG. 6 is a perspective view of the decorative housing of FIG. 5, the kitty litter box being shown completely positioned within the housing.

Turning now to FIGS. 5 and 6, a decorative housing 10 70 for the kitty litter box 10 is shown. The decorative housing 70 provides a permanent enclosure for the kitty litter box 10. In the preferred embodiment, the housing 70 is configured and adorned to resemble a human dwelling. In this manner, the decorative housing 70 provides a pleasing appearance for a cat-owner and privacy for a cat during interaction with the kitty litter 20.

The housing 70 includes an opening 72 for inserting/withdrawing the kitty litter box 10. Thus, the container 22 of a new kitty litter box 10 could be converted to the open condition, inserted through the opening 72 (see FIG. 5) and positioned within the decorative housing 70 (see FIG. 6). When the kitty litter 20 becomes sanitarily unacceptable, the kitty litter box 10 could be withdrawn through the opening 72, the container 22 converted to the closed condition and disposed, and a new kitty litter box inserted into the housing.

Figure 7:
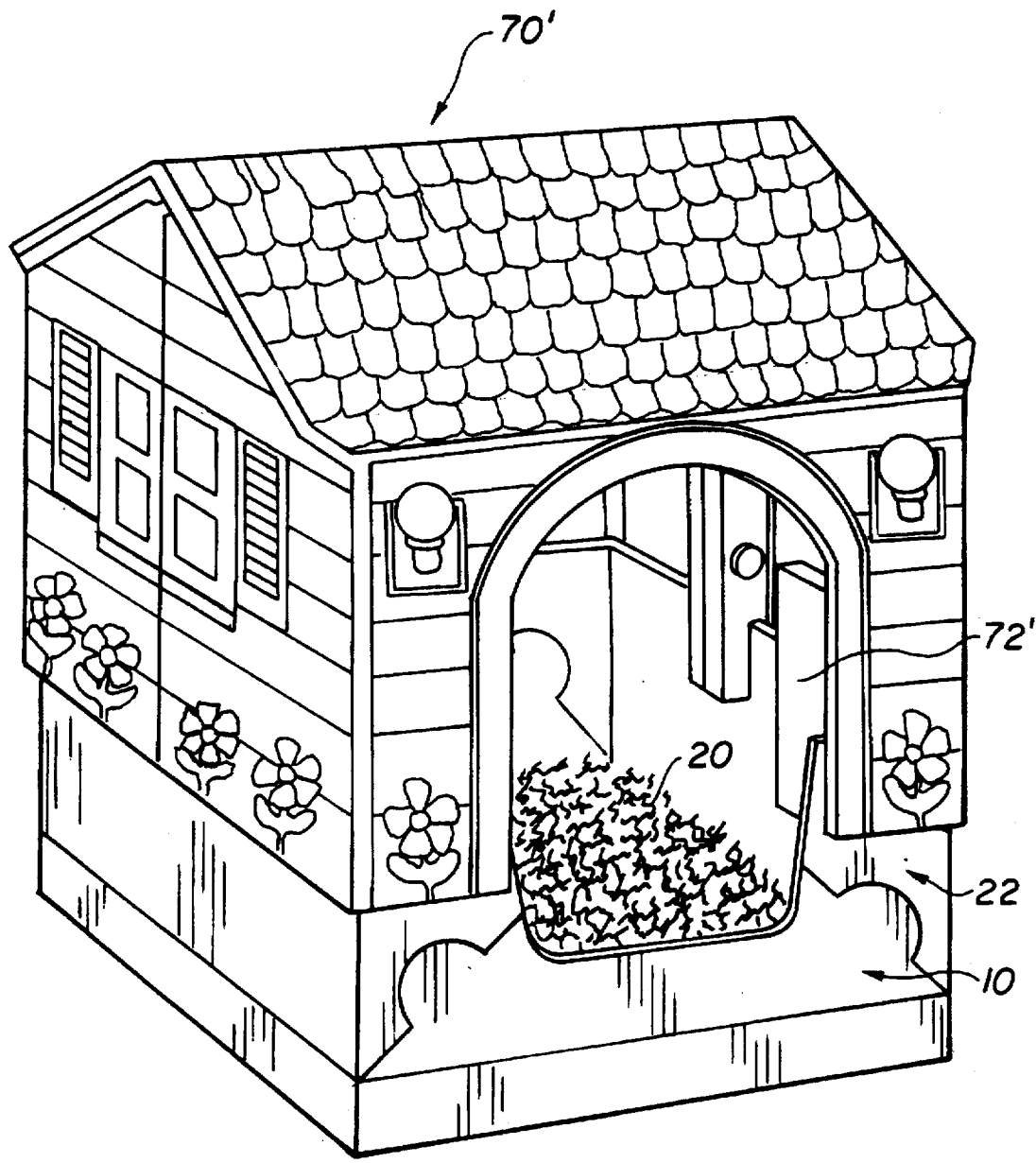
FIG. 7 is a perspective view of another form of a decorative housing for an embodiment of the kitty litter box.

An alternate form 70' of a decorative housing for the kitty litter box 10 is shown in FIG. 7 which is also configured and adorned to resemble a human dwelling. However, the housing 70' is designed to form an upper extension of the kitty litter box 10 and has an opening 72' which forms an extension of the cut-out 37.

Applicants contemplate that the kitty litter box 10, alone or in conjunction with the decorative housing 70, may be used in the homes of cat owners to replace conventional kitty litter boxes. Also, applicants believe the kitty litter box 10 would be advantageous in situations where a large number of kitty litter boxes are needed, such as at pet shops, animal shelters and/or pet shows. Moreover, the kitty litter box 10 is especially suited for traveling with cats.

Figure 8:
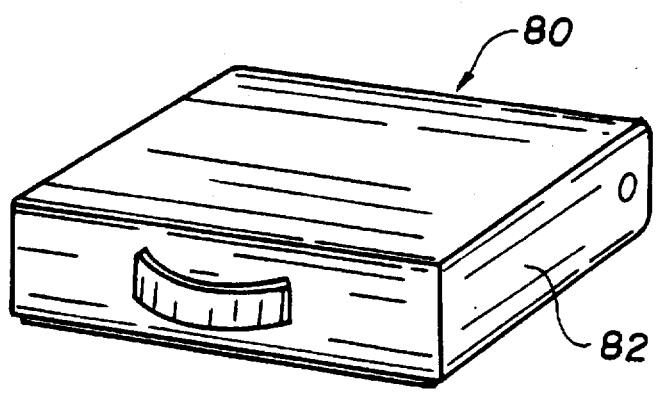
FIG. 8 is a perspective view of a kitty travel case which contains a plurality of disposable kitty litter boxes and other miscellaneous pet articles.
Figure 10:
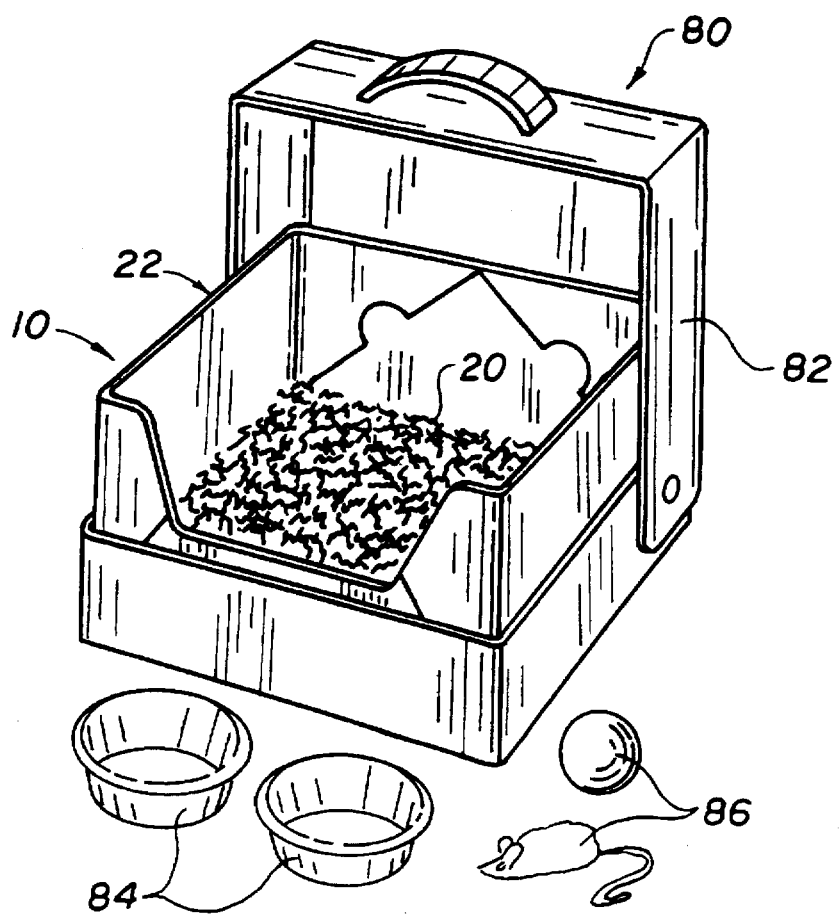
FIG. 10 is an exploded perspective view of the kitty litter travel case of FIG. 8, the case being shown with one of the disposable kitty litter boxes assembled therewith.
Figure 9:
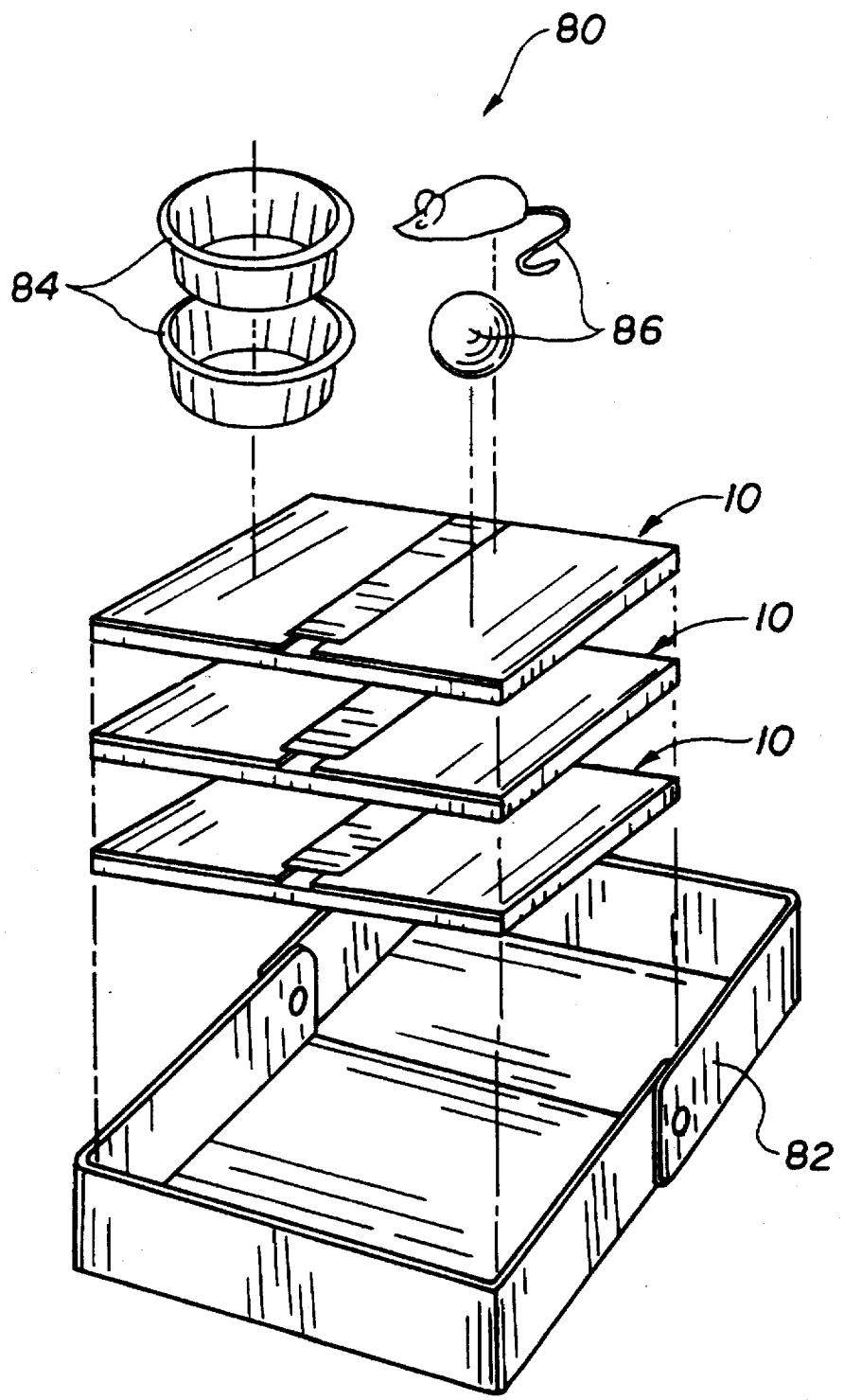
FIG. 9 is an exploded perspective view of the kitty travel case of FIG. 8.

With particular reference to travel situations, the travel set 80 shown in FIGS. 8–10 was developed. The travel set 80 includes a case 82 which is sized to efficiently accommodate a plurality of the kitty litter boxes 10, and other miscellaneous cat items, such as food/water bowls 84 and toys 86. (See FIG. 7.) As is best seen in FIG. 6, the case 82 is designed to resemble a conventional suitcase and to be easily transported in a car, plane, or other vehicle to the desired designation. Additionally, the case 82 is configured to hold an opened kitty litter box 10. (See FIG. 10.)

Figure 11:
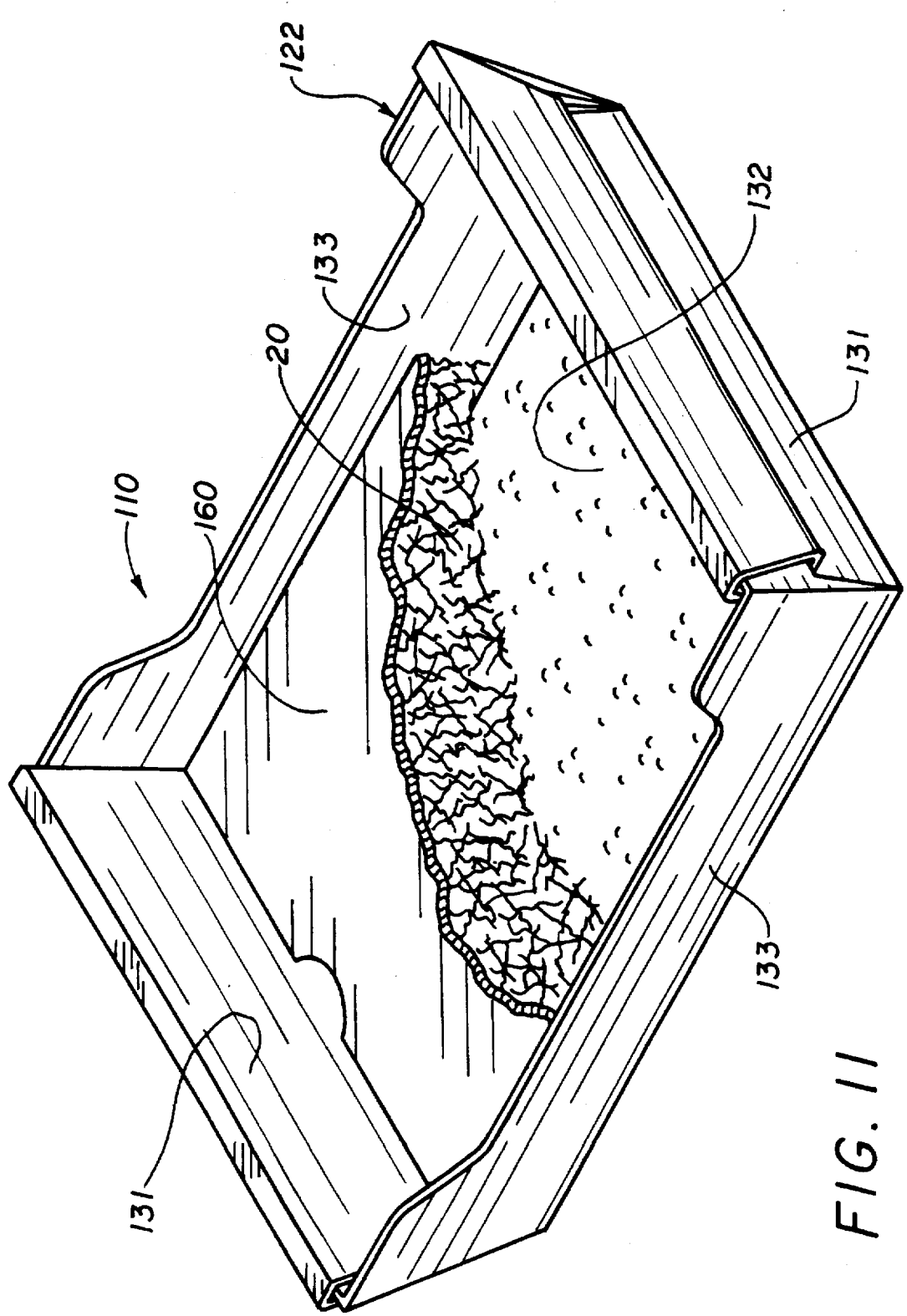
FIG. 11 is a partially cut-away perspective view of another embodiment of a kitty litter box, showing the flat cover panel enclosing the resilient paper kitty litter, which is underlain by an absorbent antibacterial sheet of paper product.
Figure 12:
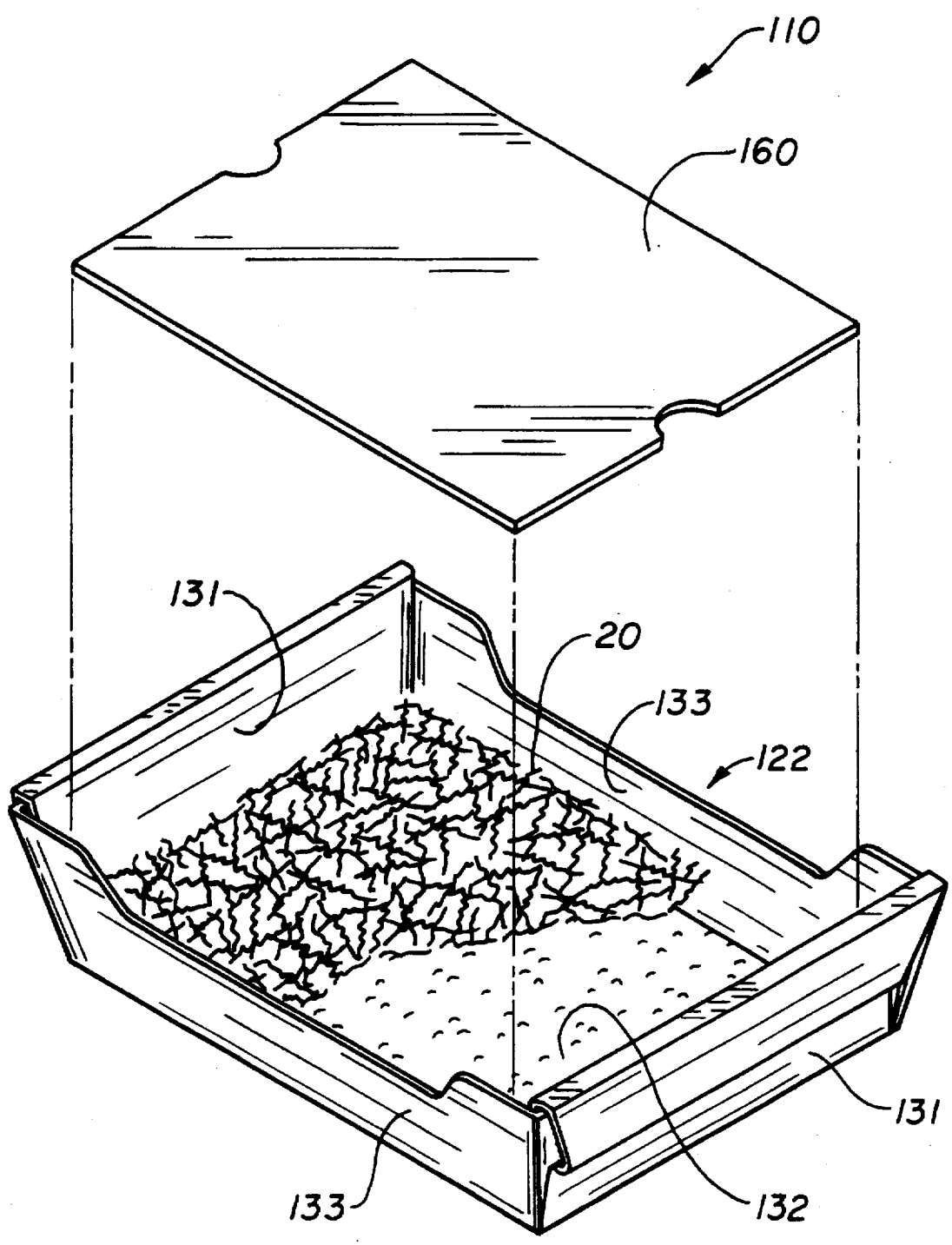
FIG. 12 is a partially exploded and cut-away perspective view of an embodiment of the container similar to that shown in FIG. 11, according to the invention.
Figure 13:
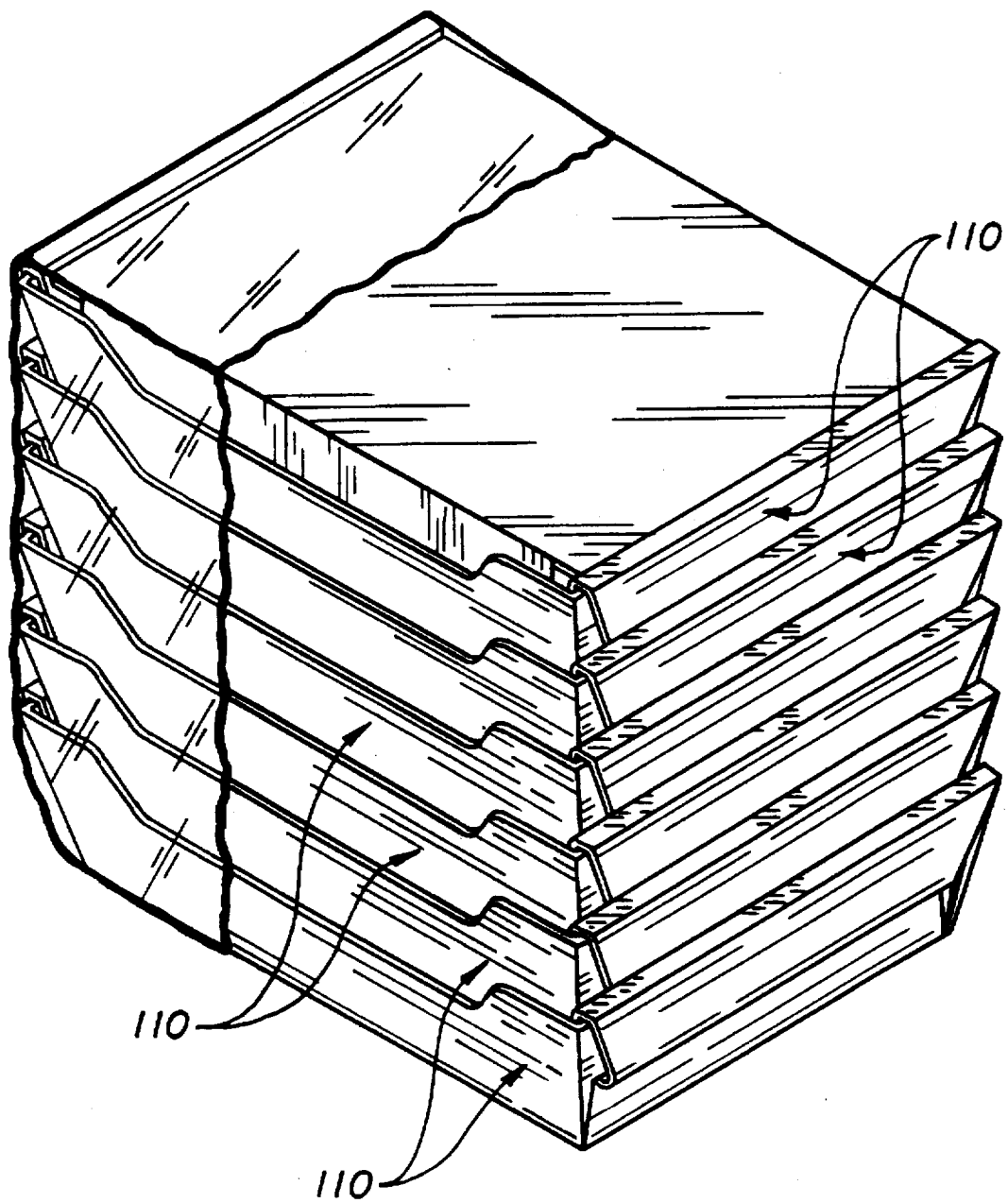
FIG. 13 is a perspective view of a nested stack of six containers according to the invention.

Referring now to another embodiment of a disposable kitty litter box, a container according to the invention is depicted in FIGS. 11–15. As was indicated for the first embodiment described above, in the present embodiment the disposable kitty litter box is convertible between a closed condition in which it forms a closed receptacle 110 (FIG. 11) and an open condition in which it forms an open receptacle 122 (FIG. 12). When the box is initially in the closed condition, the fresh kitty litter 20 is enclosed within the closed receptacle 110. When the box is in the open condition, the open receptacle 122 confines the fresh kitty litter 20 while at the same time permitting a cat access for interaction with the fresh kitty litter 20.

Thus, to supply a kitty litter box for a cat, the closed receptacle 110 is converted into an open receptacle 122 to thereby permit access to the fresh kitty litter 20. The cat may then interact with the fresh kitty litter 20 until it reaches a sanitarily unacceptable condition. Once the fresh kitty litter 20 reaches a sanitarily unacceptable condition, the open receptacle 122 is converted back into the closed receptacle 110 to thereby enclose the sanitarily unacceptable kitty litter within the container. The kitty litter box and the sanitarily unacceptable kitty litter enclosed therein may then be disposed of as a unit. In this manner, the often unpleasant and unsanitary task associated with changing kitty litter in conventional boxes is eliminated.

The disposable kitty litter box of this embodiment is made of material which is of a sufficient strength to function as a self-standing carton in its open condition. Preferably, the box is made of a paper material so that it is biodegradable and recyclable, and thus environmentally responsible. More preferably, the box is made of corrugated cardboard as this material economically provides the desired characteristics.

The disposable kitty litter box includes a set of panels and appropriate interconnections therebetween, by which the box or receptacle is formed. Specifically, when viewed in the cutaway or open condition (FIGS. 11 and 12), the open receptacle 122 comprises an inner bottom panel 132 which, as is described in more detail below, is formed of a specially treated absorbent paper material which has been additionally treated with an antibacterial agent. The open receptacle 122 additionally comprises two end panels 131 and two side panels 133. The closed receptacle 110 further comprises a flat cover panel 160 as shown in FIGS. 11 and 12. Thus the closed receptacle 110 comprises the open receptacle 122, the fresh kitty litter 20, the absorbent paper sheet material, and the cover panel 160. After the disposable kitty litter box has been used, it further includes waste material contributed by the cat or other animal user of the box.

When the receptacle 122 is converted to the closed condition (see FIG. 11), the cover panel 160 is in place as shown in FIG. 11 and forms an enclosure for the fresh kitty litter 20.

When the receptacle 122 is in an open condition (see FIG. 12), the panels 131–133 form the walls of the open receptacle 122. As is best shown in FIG. 11, the height of each of the side panels 131–133 is preferably such that it exceeds the level of resilient fresh kitty litter 20 in the receptacle 122. Thus, in the preferred container of this embodiment, the height of the side panels preferably would be approximately from two and one-half to five inches, and the height of the fresh kitty litter 20 preferably would be approximately one and one-half inches. The exact outline shape of the side panels 133 is limited only by design choice and economics. The preferred side panels 133 have the general shape shown in FIGS. 11–13.

Figure 14:
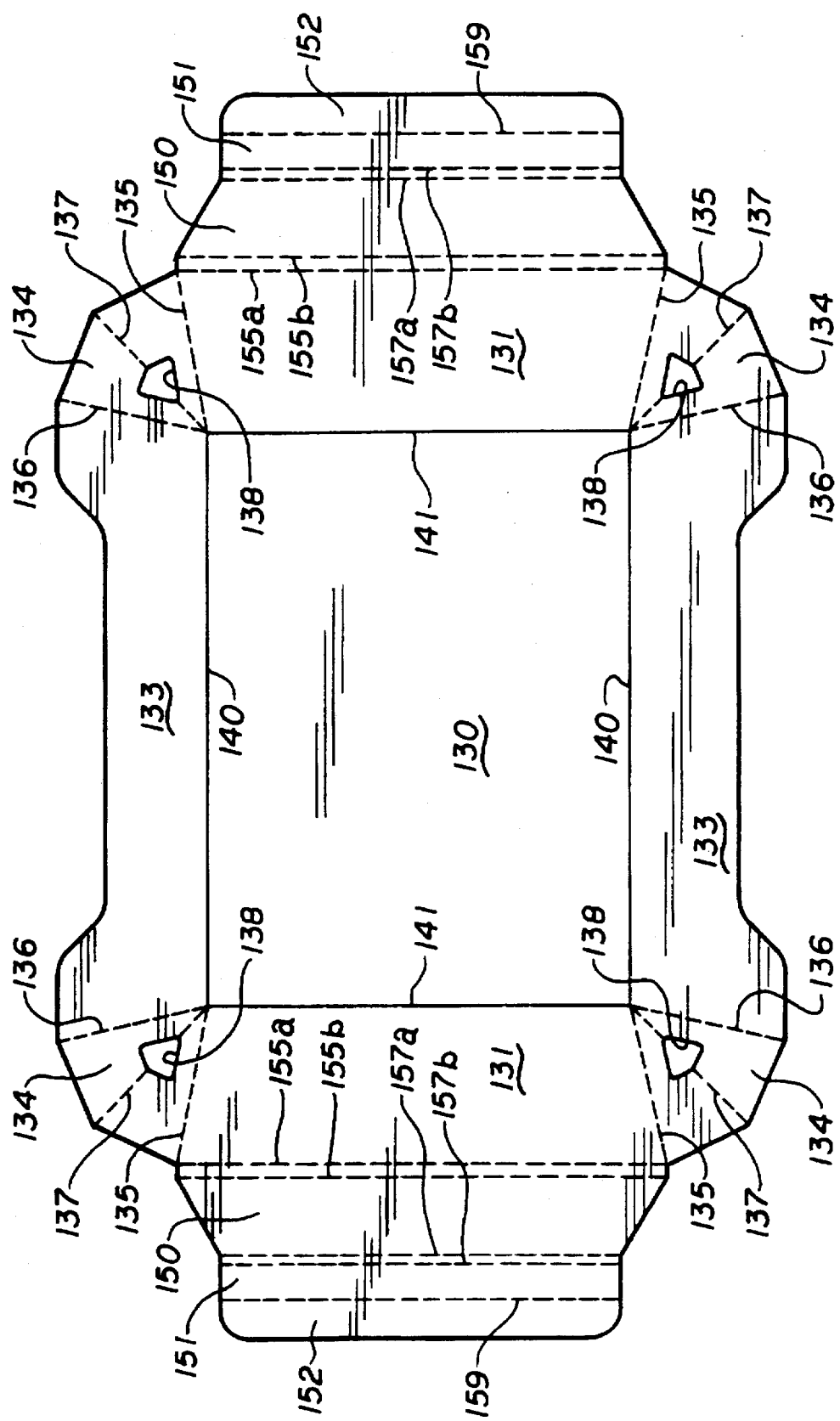
FIG. 14 is a plan view of a single sheet of cardboard from which an embodiment of the receptacle can be assembled, according to the invention.

Referring now additionally to FIG. 14, a single sheet of cardboard from which the receptacle 122 may be constructed is illustrated. As shown, the bottom panel 130 is roughly rectangular in shape. The side panels 133 and the end panels 131 are slightly trapezoidal in shape, with the smaller parallel side attached to the bottom panel 130. As a result of this configuration, the walls of receptacle 122 extend slightly vertically outward, so that the receptacle 122 has a somewhat trough-like shape, whereby the square area of the bottom panel 130 is smaller than the square area circumscribed by the upper edges of panels 131 and 133. In the single sheet of cardboard, the two side panels 133 and end panels 131 are arranged adjacent to each other around the bottom panel 130. The side panels 133 and end panels 131 are connected by connecting panels 134, filling the substantially triangular corner spaces created by the adjacent substantially rectangular side and end panels 133 and 131. The end panels 131 are integrally attached to first, second and third handle panels, 150, 151, and 152 respectively, as shown in FIG. 4. The end panels 131 are each foldably attached to the first handle panels 150 via fold lines 155a and 155b. The first handle panels 150 are each foldably attached to second handle panels 151 via fold lines 157a and 157b. The second handle panels are in turn each attached to third handle panels 152 via fold lines 159.

Figure 15A:
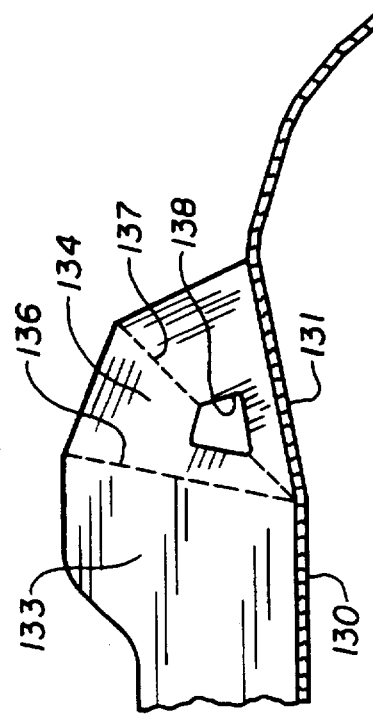
FIGS. 15A through 15E are a sectional view of the single cardboard sheet of FIG. 14, showing the steps for folding the sheet to form the receptacle according to the invention.
Figure 15B:
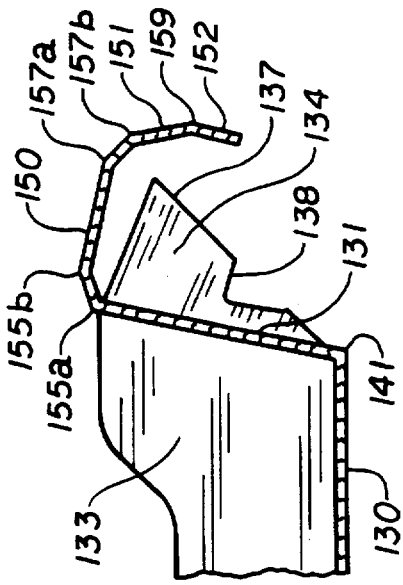
Figure 15C:
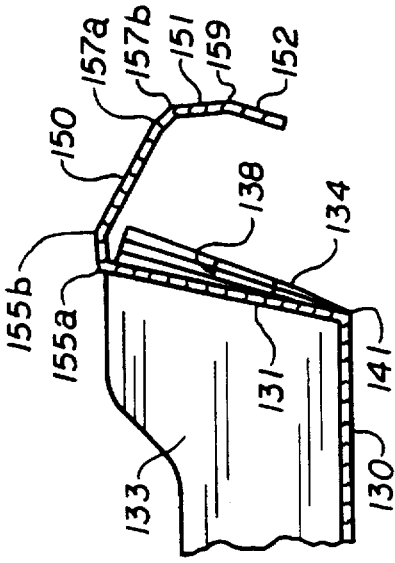

Referring now to FIGS. 15A through 15F, to assemble the receptacle 122 from the sheet of cardboard, the panels 131–133 are hinged about fold lines 140 and 141 (FIG. 15A) to form perpendicular corner intersections (FIG. 15B), with fold lines 136 meeting fold lines 135, and triangular connecting panels 134 extending outwardly from the newly-formed receptacle 122. The outwardly extending panels 134 are then folded over against end panels 131, as best shown in FIG. 15C.

Figure 15D:
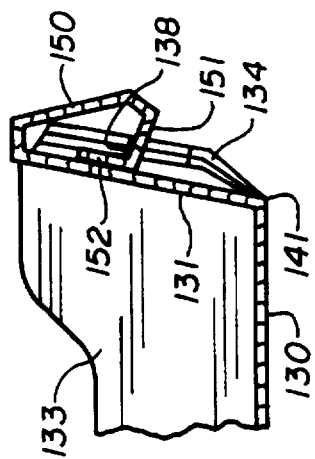
Figure 15E:
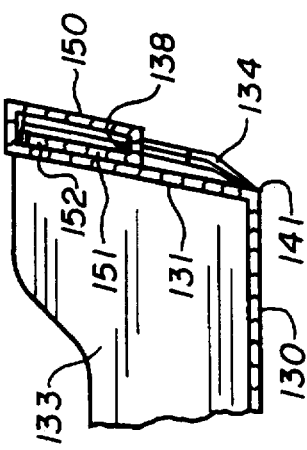

The third handle panel 152 is folded against so as to lie flat against end panel 131 as shown in FIG. 15D, as the first, second, and third handle panels, 150, 151, 152 are bent about the respective fold lines. The second handle panel 151 is then pushed upward toward the third panel 152 to the position shown in FIG. 15E, in which both the second and third handle panels, 151 and 152, are in maximum contact with the end panels 131. At this point, the second handle panel 151 is in releasable locking engagement with the apertures 138 in each adjacent triangular panel 134, thereby holding the receptacle 122 in an upright, box-like functional condition, as shown in FIG. 15E.

The preferred shape of the container allows multiple containers to be nestably stacked. In this second preferred embodiment, the length and width of the bottom of a first container 110 fits easily within the open space above the fresh kitty litter 20 defined by the portion of the walls extending above the cover panel 160, of a second, lower container 110, whereby the bottom of the first container 110 preferably actually rests upon the cover panel 160 and partially within the walls of the lower container 110 with which it is nested. Thus, while the container 110 may have a height of, e.g., four inches, when the container is nestably stacked in accordance with the invention, the container contributes only about one and three-quarters inch to the total height of a nested stack of such containers.

In this embodiment of the invention, to convert the disposable kitty litter box 110 between the open and closed conditions, the user simply removes or replaces top panel 160 within the receptacle 122 formed by panels 131 and 133. When in the closed condition, top panel 160 will be in contact with the fresh kitty litter 20, and will resiliently compress fresh kitty litter 20 somewhat.

Due to the resilient nature of fresh kitty litter 20, if the fresh kitty litter 20 of the present invention is compressed, when released it will assume a larger volume. This feature provides an additional significant benefit to the manufacturer, dealers, and users of the disposable kitty litter box of this invention, since it provides for a much more compact container. These benefits are provided in conjunction with an antibacterial absorbent sheet, which is preferably disposed in the bottom of receptacle 122, covered with fresh kitty litter 20, to further increase the sanitary nature of the disposable kitty litter box. The compactability, in conjunction with the stackability and nestability of the present invention, combine to provide unexpected benefits in cost savings and space savings during storage and shipping, which when considered with the lightweight nature of this invention, easy-to-use disposable kitty litter box.

Both embodiments of the invention described herein preferably include an absorbent antibacterial sheet 132, made of a paper material of enhanced liquid absorbing character. Preferably the sheet 132 is placed between the bottom panel 30 or 130 and the fresh kitty litter 20, as depicted in FIGS. 11 and 12.

The most preferred absorbent paper for sheet 132 has approximately 28 pound weight, is unlined, and has been treated with a broad-spectrum antibiotic or antibacterial material such as neomycin, and has been treated with an odor reducing or neutralizing agent. The quantity of antibiotic or antibacterial material is sufficient to retard the growth of any bacterial species present in such use, for a period of time before the kitty litter box reaches a sanitarily unacceptable condition. The preferred antibiotic is neomycin. The preferred odor reducing agent includes acidic materials, such as malic acid or organic acid sulfonates, and cosolvent materials, such as ethanolamine or diethanolamine. The materials combine to reduce the level of volatile odorant compounds in the kitty litter 20 during the time it is made available for use by a cat or other animal. The odor reducing or neutralizing material may further include fragrance compounds to provide masking of odors not otherwise eliminated.

The most preferred absorbent paper material 132 is 28 pound Shoksorb with neomycin, available from Kieffer Paper Mills, Inc. Brownstown, Ind. 47220. In the most preferred embodiment, the absorbent paper 132 is treated with Epoleon N-100-65-2, available from Epoleon Corporation, Tokyo, Japan, as the odor reducing or neutralizing material. Epoleon comprises an aqueous solution of phenolsulfonate, malic acid and diethanol amine.

Once the fresh kitty litter 20 reaches a sanitarily unacceptable condition, the receptacle 122 may be converted back into the closed receptacle 110 by placing the top panel 160 over the sanitarily unacceptable kitty litter 20. In this embodiment of the invention, to convert the container between the open and closed conditions, the user simply removes or replaces top panel 160 within the receptacle 122 thereby sealing the sanitarily unacceptable kitty litter within the receptacle 122. The container and the sanitarily unacceptable kitty litter enclosed therein may then be disposed of as a unit.

Applicants contemplate that the disposable kitty litter box may be used in the homes of cat owners to replace conventional kitty litter boxes. Also, applicants believe the disposable kitty litter box would be advantageous in situations where a large number of kitty litter boxes are needed, such as at pet shops, animal shelters and/or pet shows, particularly due to the stackable and nestable features of the present embodiment of the invention.

One may now appreciate that the present invention provides a lightweight, nestably stackable kitty litter box containing compactable, resilient, absorbent fresh kitty litter 20, which may be compactly stored as a closed receptacle 110 until ready for use, converted into an open receptacle 122 for interaction with a cat, and then converted back into a closed receptacle 110 for convenient and sanitary disposal purposes. Although the invention has been shown and described with respect to certain preferred embodiments, it is obvious that equivalent alterations and modifications will occur to others skilled in the art upon the reading and understanding of this specification. The present invention includes all such equivalent alterations and modifications and is limited only by the scope of the following claims.

What is claimed is:

1. A disposable kitty litter box comprising a container and fresh kitty litter enclosed within the container;

the container being convertible between a closed condition in which it encloses the kitty litter, and an open condition in which it forms an open receptacle for use of the kitty litter;

the fresh kitty litter comprising a plurality of paper strips treated with a neutralizing agent.

2. A disposable kitty litter box as set forth in claim 1 wherein the fresh kitty litter has a density of approximately 0.01. to 0.100 ounces per cubic inch.

3. A disposable kitty litter box as set forth in claim 1 wherein the container includes a set of panels and interconnections between at least some of the panels which allows the container to convert from the closed receptacle to an open-topped receptacle and from the open-top receptacle to the closed receptacle.

4. A disposable kitty litter box as set forth in claim 1 wherein the container includes a set of panels forming the open receptacle and a cover panel which, when placed over the open receptacle, encloses the kitty litter within the container.

5. A disposable kitty litter box as set forth in any of claims 1-4 wherein the plurality of paper strips are accordion-folded resilient paper strips.

6. A disposable kitty litter box as set forth in claim 5 wherein the container is made of corrugated cardboard.

7. A disposable kitty litter box as set forth in claim 6 wherein the fresh kitty litter is biodegradable and recyclable.

8. A disposable kitty litter box as set forth in claim 5 wherein the fresh kitty litter is biodegradable and recyclable.

9. A disposable kitty litter box comprising a container and fresh kitty litter enclosed within the container and an absorbent, anti-bacterial sheet positioned beneath the fresh kitty litter:

the container being convertible between a closed condition in which it encloses the kitty litter, and an open condition in which it forms an open receptacle for use of the kitty litter;

the fresh kitty litter comprising a plurality of paper strips treated with a neutralizing agent.

10. A disposable kitty litter box as set forth in claim 9, wherein the sheet is treated with a neutralizing agent.

11. A disposable kitty litter box as set forth in claim 9 or claim 10 wherein the plurality of paper strips are accordion-folded resilient paper strips.

12. A disposable kitty litter box as set forth in claim 9 wherein the fresh kitty litter has a density of approximately 0.01 to 0.100 ounces per cubic inch.

13. A disposable kitty litter box as set forth in claim 9 wherein the container includes a set of panels and interconnections between at least some of the panels which allows the container to convert from the closed receptacle to an open-topped receptacle and from the open-top receptacle to the closed receptacle.

14. A disposable kitty litter box as set forth in claim 9 wherein the container includes a set of panels forming the open receptacle and a cover panel which, when placed over the open receptacle, encloses the kitty litter within the container.

15. A disposable kitty litter box as set forth in any of claims 12–14, wherein the sheet is treated with a neutralizing agent.

16. A disposable kitty litter box as set forth in any of claims 12–15 wherein the plurality of paper strips are accordion-folded resilient paper strips.

17. A disposable kitty litter box as set forth in claim 15 wherein the plurality of paper strips are accordion-folded resilient paper strips.

18. A method of supplying a kitty litter box for a cat, said method comprising the steps of:

providing a container of fresh kitty litter comprising a plurality of paper strips treated with a neutralizing agent;

allowing the cat to interact with the fresh kitty litter until it reaches a sanitarily unacceptable state;

enclosing the sanitarily unacceptable kitty litter in the container; and disposing of the container, and the sanitarily unacceptable kitty litter, as a unit.

19. A method as set forth in claim 18, wherein the fresh kitty litter has a density of approximately 0.01 to 0.100 ounces per cubic inch.

20. A method as set forth in claim 18 wherein the container is convertible between a closed condition and an open condition in which it forms an open receptacle;

wherein said providing step comprises the step of enclosing fresh kitty litter in the container when it is in the closed condition; and wherein said allowing step comprises thereafter converting the container into the open condition to form the open receptacle to thereby allow the cat access to the fresh kitty litter.

21. A method as set forth in claim 20 wherein said enclosing step includes the steps of:

placing the container in the open condition whereby it forms the open receptacle;

inserting the fresh kitty litter into the open receptacle; and thereafter converting the container into the closed condition whereby it forms the closed receptacle which encloses the fresh kitty litter.

22. A method as set forth in claim 20 wherein the container includes a set of panels and interconnections between at least some of the panels which allows the container to convert from the closed receptacle to an open-topped receptacle and from the open-top receptacle to the closed receptacle.

23. A method as set forth in claim 20 wherein the container includes a set of panels forming the open receptacle and a cover panel which converts the open receptacle to a closed condition.

24. A method as set forth in any of claims 18–23 wherein the plurality of paper strips are accordion-folded resilient paper strips.

25. A method as set forth in claim 24 wherein the container is made of corrugated cardboard.

26. A method as set forth in claim 25 wherein the fresh kitty litter is biodegradable and recyclable.

27. A method as set forth in claim 24 wherein the fresh kitty litter is biodegradable and recyclable.

28. A method of supplying a kitty litter box for a cat, said method comprising the steps of:

providing a container of fresh kitty litter comprising a plurality of accordion-folded paper strips treated with a neutralizing agent; and allowing the cat to interact with the fresh kitty litter until it reaches a sanitarily unacceptable state.

29. A method as set forth in claim 28, wherein the fresh kitty litter has a density of approximately 0.01 to 0.100 ounces per cubic inch.

30. A disposable kitty litter box comprising a container and fresh kitty litter enclosed within the container;

the container being convertible between a closed condition in which it encloses the kitty litter, and an open condition in which it forms an open receptacle for interaction by a cat as a kitty litter box;

the fresh kitty litter comprising a plurality of paper strips treated with a neutralizing agent.

* * * * *